(12) United States Patent
Leach

(10) Patent No.: US 8,147,758 B2
(45) Date of Patent: *Apr. 3, 2012

(54) WATER HARDNESS SENSOR SYSTEM

(75) Inventor: Andrew Michael Leach, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 1146 days.

This patent is subject to a terminal disclaimer.

(21) Appl. No.: 11/473,867

(22) Filed: Jun. 23, 2006

(65) Prior Publication Data
US 2007/0297945 A1 Dec. 27, 2007

(51) Int. Cl.
*G01N 21/00* (2006.01)
(52) U.S. Cl. .................................... 422/82.05
(58) Field of Classification Search .............. 422/82.05
See application file for complete search history.

(56) References Cited

U.S. PATENT DOCUMENTS

| | | | | |
|---|---|---|---|---|
| 3,895,913 A * | 7/1975 | Bockowski et al. | .......... | 436/112 |
| 3,975,160 A | 8/1976 | Bohl et al. | | |
| 4,205,953 A * | 6/1980 | Miller | .............. | 436/50 |
| 4,275,448 A * | 6/1981 | Le Dall | ............. | 700/271 |
| 4,871,679 A * | 10/1989 | Tanaka et al. | ............. | 436/79 |
| 5,039,225 A * | 8/1991 | Uekusa | .............. | 356/448 |
| 5,418,143 A * | 5/1995 | Zweig | .............. | 435/13 |
| 6,190,611 B1 * | 2/2001 | Tachino et al. | ............. | 422/61 |
| 6,599,748 B1 * | 7/2003 | Nakajima et al. | ............. | 436/39 |
| 6,783,666 B2 * | 8/2004 | Takeda et al. | ............. | 210/96.1 |
| 6,814,872 B2 | 11/2004 | Rawson | | |
| 7,202,090 B2 * | 4/2007 | Mitsumoto | ............. | 436/73 |
| 7,651,663 B2 * | 1/2010 | Ayala et al. | ............. | 422/82.09 |
| 2007/0295665 A1 * | 12/2007 | Ayala et al. | ............. | 210/670 |

* cited by examiner

*Primary Examiner* — Lore Jarrett
(74) *Attorney, Agent, or Firm* — Mary Louise Gioeni

(57) ABSTRACT

A sensor including a substrate and a sensing element disposed on a substrate is provided. The sensing element includes a sensing matrix in contact with a flow of water, an indicator for one or more chemical species in the flow of water, and a selectivity component that reacts reversibly with the one or more chemical species. The sensor also includes a light source configured to direct light through the substrate and the sensing element. The sensor further includes a light detector configured to receive transmitted light from the substrate and the sensing matrix and to generate a signal representative of selective wavelengths of the light indicative of the one or more chemical species in the flow of water.

9 Claims, 9 Drawing Sheets

WATER HARDNESS SENSOR SYSTEM

BACKGROUND

The invention relates generally to water treatment, and, more particularly, to a technique for measuring hardness of water and using such measurements.

Industrial and residential water systems draw water from a number of potential sources including wells, rivers and reservoirs. These sources have varied levels of inherent water hardness. Water hardness is generally a function of calcium (Ca) and magnesium (Mg) concentration. It is measured in grains per gallon or milligrams per liter of calcium carbonate and can vary from 0 to greater than 50 grains per gallon depending upon the water source.

Calcium and magnesium species responsible for hardness in water also account for much of the inorganic scaling and fouling of water in industrial and residential water systems and appliances. Fouling of water has been observed in residential environments, such as, for example, in sinks, tubs, dishes, glassware and also hot water heaters. Similarly, in industrial systems, fouling of industrial boiler systems and heat exchangers has been observed. Hardness of water also commonly affects performance of detergents in cleaning or washing applications. Elevated levels of water hardness also affect the performance and maintenance of water softeners.

Some of the widely used techniques for measuring hardness of water include colorimetric, fluorescent assays that measure concentrations of calcium and magnesium. Colorimetric and fluorescent assays are tested by addition of liquid or solid reagents to a water sample that is buffered to an appropriate pH. The reagent addition either includes a one step addition, wherein a final color is measured, or is performed as a titration, and wherein a point of color transition is determined. The assays are then measured with a photometric detector followed by disposal of the sample and spent reagents.

However, the colorimetric assays and fluorescence assays are relatively labor intensive to test and are principally used for periodic or point measurements. In addition, the reactions involved in such testing are irreversible and the sample and test strips often used for such testing are thus disposed of following the measurements. This makes their use in industrial, commercial, and particularly consumer appliances impractical.

Further, the availability of water of variable hardness commonly requires a user of home appliances, such as clothes washers and dishwashers, to manually adjust the amount of detergent to achieve optimal cleaning of clothes and dishes. In general, the quantity of detergent required increases with the hardness of water so as to achieve optimal performance. However, manually adjusting the amount of detergent based on an assumption that is likely to incorrectly reflect actual hardness of water commonly leads to waste of detergent or, conversely, to the use of insufficient detergent when hardness is particularly elevated.

In another application, such as controlling regeneration of a water softener, it has been assumed that hardness levels of influent water to a water softener are constant. However, for all practical purposes, the hardness level of influent water is a variable quantity. Further, regeneration control systems of water softeners commonly measure volume of water treated as the only control variable. Hence, varying hardness levels of water can adversely affect performance of the water softeners in a manner not compensated for by the control algorithms.

Hence, an improved technique for measuring hardness of water is needed to address the aforementioned issues. It would also be desirable to provide a technique to monitor hardness of influent water in real time in home appliances and water softeners for optimal performance.

BRIEF DESCRIPTION

In accordance with one aspect of the invention, a sensor for detecting hardness in water is provided. The sensor includes a substrate and a sensing element disposed on the substrate. The sensing element includes a sensing matrix in contact with a flow of water, an indicator for one or more chemical species in the flow of water, and a selectivity component that reacts reversibly with the one or more chemical species. The sensor also includes a light source configured to direct light through the substrate and the sensing element. The sensor further includes a light detector configured to receive transmitted light from the substrate and the sensing matrix and to generate a signal representative of selective wavelengths of the light indicative of the one or more chemical species in the flow of water.

In accordance with another aspect of the invention, the sensor includes a substrate as a transparent tube that is configured to receive a flow of water. The sensor includes a sensing element disposed on an internal surface of the tube and including a sensing matrix in contact with a flow of water during operation, an indicator for one or more chemical species in the flow of water, and a selectivity component that reacts reversibly with the one or more chemical species. As before, the sensor also includes a light source configured to direct light through the substrate and the sensing element, and a light detector configured to receive transmitted light from the substrate and the sensing matrix and to generate a signal representative of selective wavelengths of the light indicative of the one or more chemical species in the flow of water.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the present invention provide a sensor suitable for measuring hardness of water based upon an optical technique. The sensor may be installed inline with a flow of water. Further, embodiments of the present invention provide applications for the sensor. In a specific example, applications are provided of the sensor in a cleaning appliance such as a clothes washing machine or dish washing machine and in a controller for regeneration of a water softener.

Figure 1:
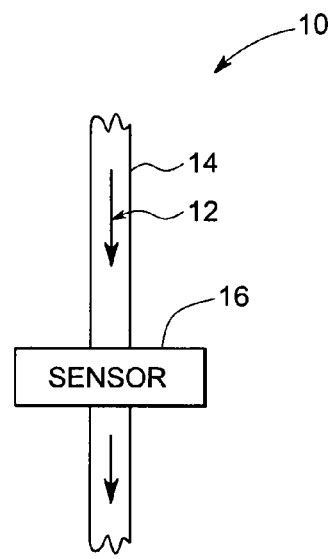
FIG. 1 is a diagrammatic illustration of an inline sensor disposed to receive a flow of water in accordance with the invention.

Turning now to the drawings, FIG. 1 is a diagrammatic illustration of a hardness sensor assembly 10 in accordance with aspects of the invention. A flow of water 12 runs through a pipe system 14 and passes over a sensor 16 disposed in-line with the flow of water 12. The sensor 16 that detects hardness in the flow of water 12. The sensor 16 is described in more detail with reference to FIG. 2.

Figure 2:
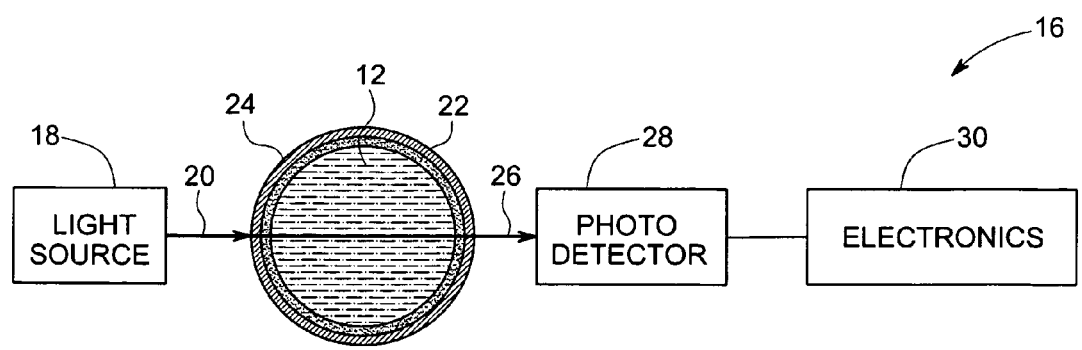
FIG. 2 is a diagrammatic representation of the sensor of FIG. 1 illustrating various components of the sensor in accordance with the invention.

In an exemplary embodiment of the invention as shown in FIG. 2, the sensor 16 includes a light source 18 designed to direct light 20 onto a sensing element 22 that is disposed on a substrate 24. In the illustrated embodiment of the invention, the substrate 24 may include a transparent tube. The sensing element 22 may be disposed on an internal surface of the tube. As shown in FIG. 1, the sensor 16 is disposed in-line with the flow of water 12 as referenced in FIG. 1 such that the sensing element 22 is in contact with the flow of water 12. The transmitted light 26 from the sensing element 22 is directed onto a photodetector 28. The transmitted light 26 is used to generate a signal representative of selective wavelengths of the light indicative of one or more chemical species in water 12. An electronic assembly 30 is used to analyze signal from the photodetector 28 thus giving a measure of hardness in the water 12. The measure of hardness of water may be incorporated into feedback control systems. The sensing element 22 may include chemical reagents that react reversibly with one or more chemical species in water 12. Sensor geometry used in the present embodiment is one of many possible combinations of sensor components. Alternative geometries may differ in the location of the sensor element 22, or the shape of substrate 24, or the relative position of the light source 18 and photodetector 28. Non-limiting examples of alternate geometries include: (1) placement of a sensing element 22 coated on substrate 24 in the center of the water 12 path; (2) a square or rectangular substrate 24; (3) placement of the light source 18 and photodetector 28 adjacent to one another such that light 20 and 26 follow a path defined by an angle that may range from 0 to 360 degrees. In an exemplary embodiment of the invention, the one or more chemical species in water 12 to be detected may include calcium and magnesium. In another exemplary embodiment of the invention, non-limiting examples of the substrate 24 may include a polymer, such as polycarbonate, polyethylene, polymethylmethacrylate, cyclicpolyolefin, and nylon, or glass.

Figure 3:
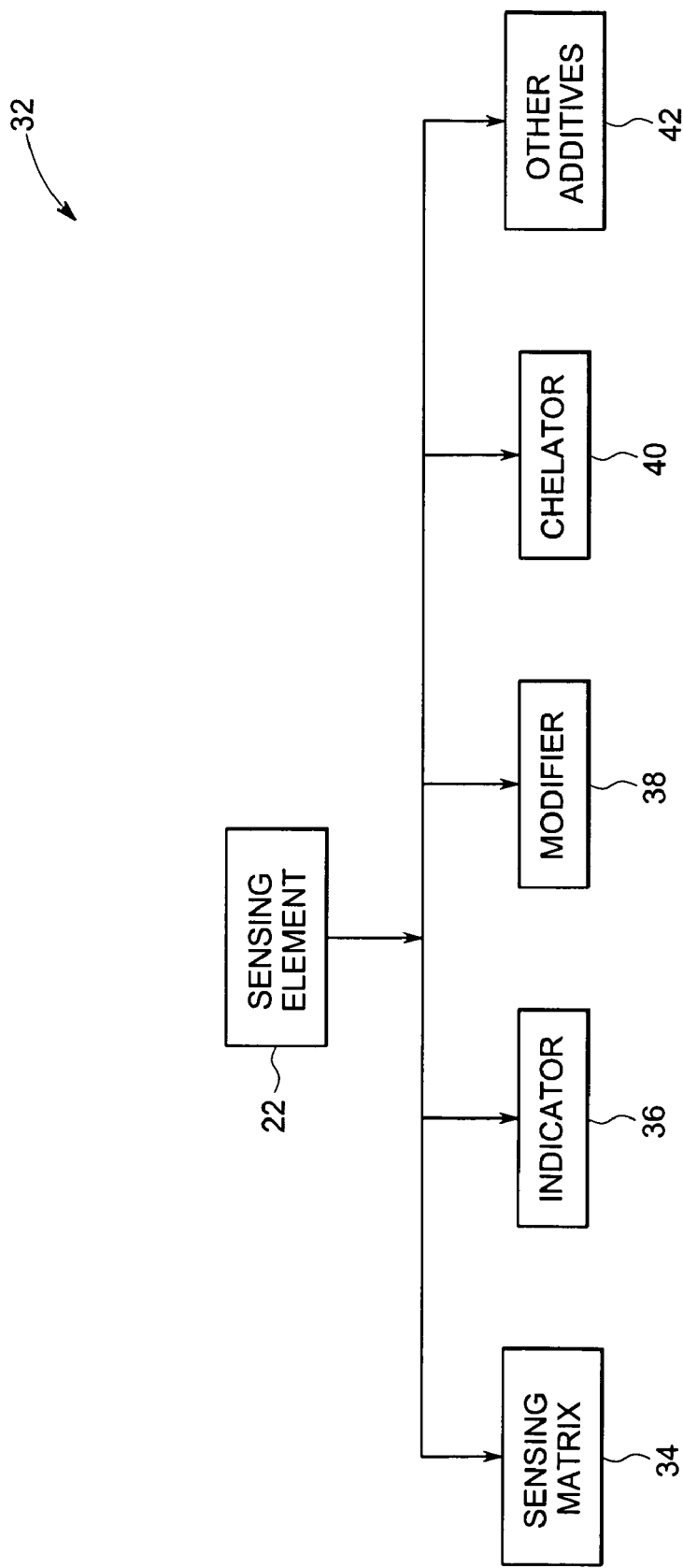
FIG. 3 is a block diagram representation of the sensing element in FIG. 2 illustrating various components of the sensing element in accordance with the invention.

FIG. 3 is a block diagram of the sensing element 22 shown in FIG. 2. The sensing element 22 includes components that include a sensing matrix 34, one or more indicators 36 and one or more modifiers 38. The sensing element 22 may also include one or more chelators 40 that react selectively and sensitively to one or more chemical species such as calcium and magnesium in the flow of water 12 as referenced to in FIG. 1. The sensing element 22 may further include other additives 42 that may alter response characteristics towards the one or more chemical species in the flow of water 12. The sensing matrix 34 enables an environment in which chemical reagents including the indicators 36, modifiers 38, chelator 40 and other additives 42 react with the one or more chemical species in the flowing water. The matrix also provides protection of the chemical reagents from the water 12. The sensing matrix 34 may be robust to water conditions and allow chemical reagents to react reversibly and selectively towards the one or more chemical species. In an example, the sensing matrix 34 may include at least one from a group comprising sol-gels, polymers and hydrogels.

The indicators 36 as described above, bind selectively to the one or more chemical species in water. For example, the indicators 36 may bind the chemical species together with equal or varied levels of affinity. Presently contemplated indicators 36 may include, but are not limited to calmagite, EBT, xylidyl blue and murexide. The modifiers 38 are chemical reagents that modify internal pH of the sensor element 22 enabling the indicators 36 to react selectively and sensitively to the chemical species in the water. Presently contemplated modifiers 38 may include para-toluene sulfonic acid and polyethyleneimine (PEI). The chelators 40 may be configured to selectively alter availability of the chemical species to bind with the indicators 36. As an example, the chelator 40 may include 8-hydroxyquinoline that reduces response of the sensing element 22 to magnesium relative to calcium in water. The other additives 42 may include additional chemical reagents that further modify response characteristics of the sensing element 22.

Figure 4:
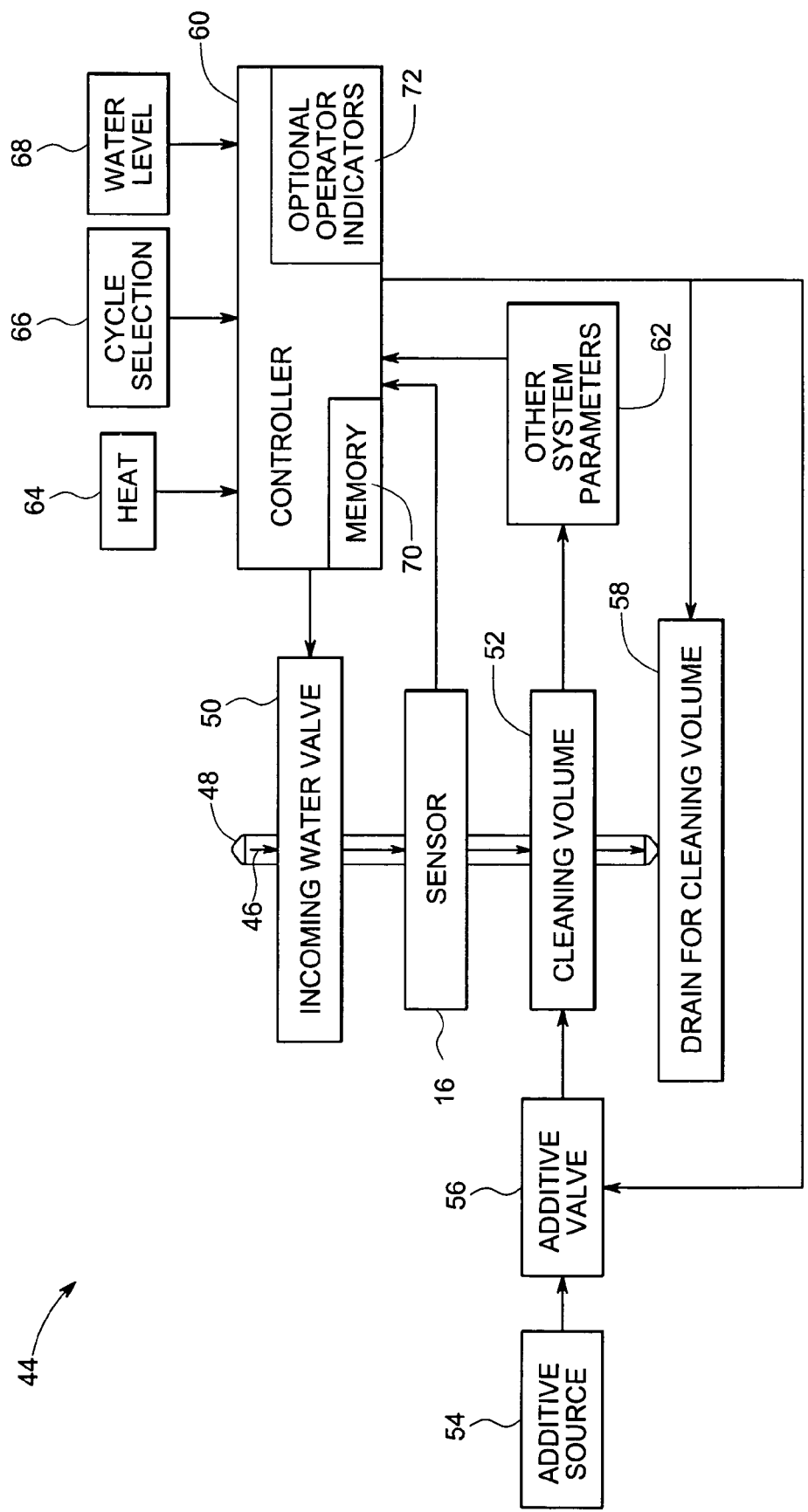
FIG. 4 is a block diagram representation of a cleaning appliance employing a water hardness sensing system in accordance with the invention.

FIG. 4 is a block diagram of an appliance system 44 using water in accordance with aspects of the invention. An incoming flow of water 46 that may be used for washing passes through a pipe system 48. The flow of water 46 passes through an incoming water valve 50 that controls the volume of water introduced into the cleaning appliance system 44. The appliance system 44 includes a sensor 16 of the type shown in FIG. 2 in-line with the flow of water 46. The sensor 16 may be installed in-line with the flow of water 46 or may be a hand-held sensor. Further, the flow of water 46 passes into a cleaning volume 52 in which washing is performed (e.g., a drum or space in which clothing, dishes, and so forth are placed). An additive source 54, such as a detergent, may be injected or introduced into the cleaning volume 52 after passing through an additive valve 56. Alternatively, in some embodiments, the additive may be injected manually. Water that is used for cleaning in the cleaning volume 52 may be drained out through a drain 58. The appliance system 44 also includes a processor or controller 60 that receives a signal indicative of hardness of the incoming flow of water 46 from the sensor 16. The controller 60 may include inputs for system parameters 62 such as amount of turbidity from the cleaning volume, heat or temperature 64, cycle selection 66 and water level to be introduced 68. The controller 60 may also include a memory circuit 70 that is configured to relate a degree of concentration of a chemical species in the incoming flow of water 46 and a degree of hardness of the incoming flow of water 46 using a look-up table, as well as storing a control program for regulating operation of the overall cleaning system. The controller 60 may further include one or more operational indicators 72. To provide for periodic monitoring of hardness of water, a strip, a button or other similar surface that contains a hardness-sensitive dye can be periodically indexed to the operational indicators 72. This can be subsequently used again to analyze the hardness of the water. For example, the operational indicators 72 may indicate to an operator an appropriate amount of additive to be used, such as for systems in which the additive is introduced manually. Some non-limiting examples of the appliance system 44 include a clothes washing machine, a dishwasher, pressure driven reverse osmosis membrane, a water purifier and humidifier.

Figure 5:
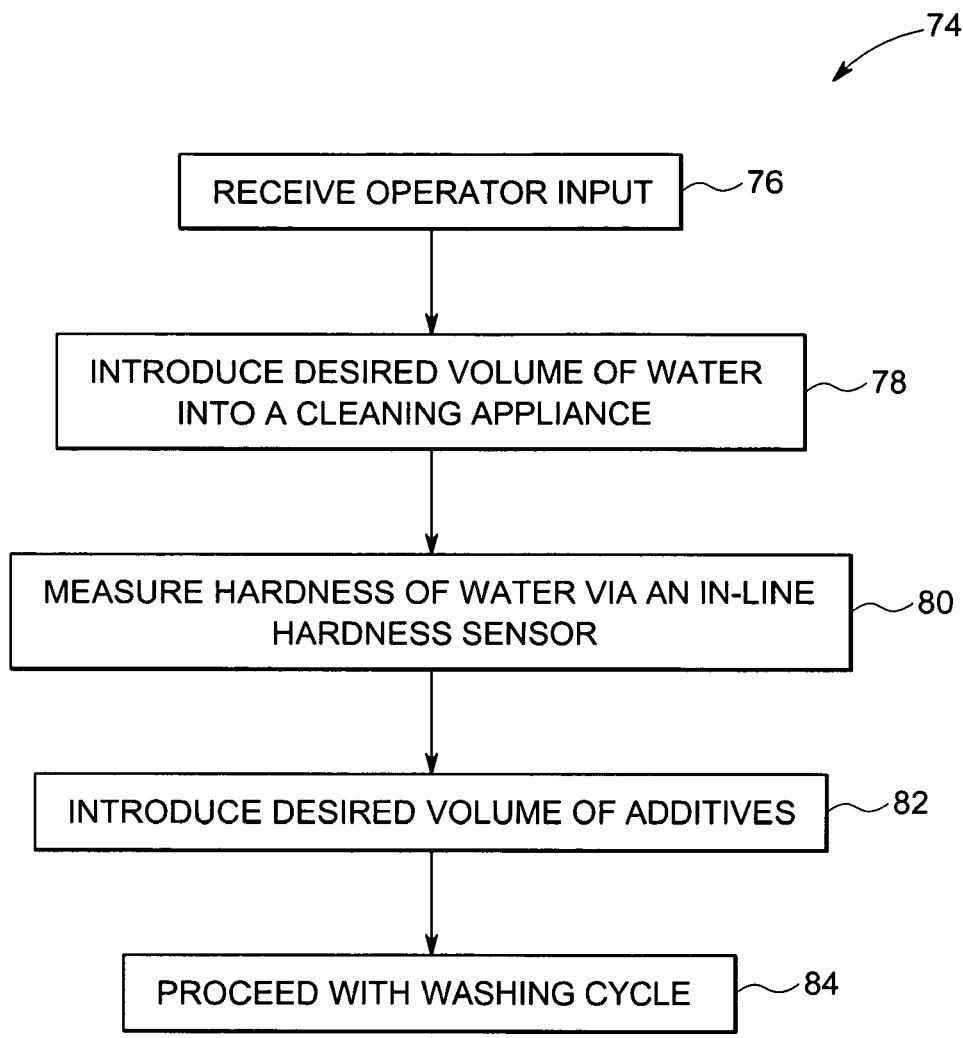
FIG. 5 is a flow chart illustrating exemplary steps for a method of operation of the cleaning appliance of FIG. 4 in accordance with the invention.

FIG. 5 is a flow chart 74 illustrating exemplary steps in a method for operating an appliance system using water with an in-line sensor in accordance with an embodiment of the present invention. The method includes receiving an operator input at step 76. Depending on the operator input, a desired volume of water is introduced into the cleaning appliance system at step 78. The water passes through an in-line hardness sensor that measures hardness of the water at step 80. A desired volume of additives is then introduced into the cleaning appliance system at step 82. After the additives are introduced, the method 74 includes proceeding with the rest of the washing cycle at step 84.

Figure 6:
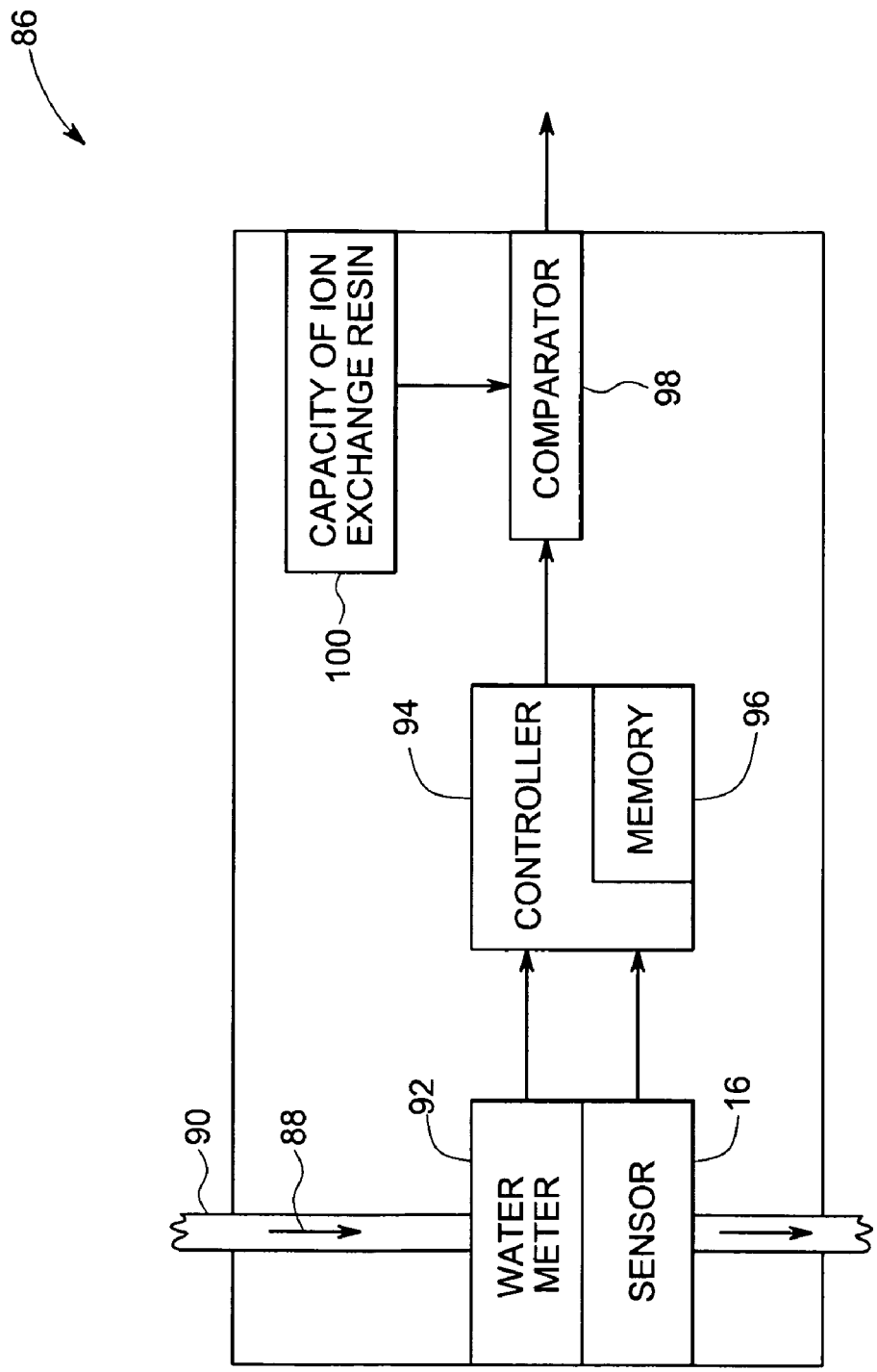
FIG. 6 is a block diagram representation of a regeneration system in a water softener utilizing a water hardness sensing system in accordance with the invention.

In another exemplary embodiment of the present invention as shown in FIG. 6, a system 86 to control regeneration of a water softener with an in-line sensor is illustrated. An incoming flow of water 88 that may be used for washing passes through a pipe system 90. The incoming flow of water 88 passes through a water meter 92 that may output a signal indicative of volume of incoming water received by the water softener. Further, the incoming flow of water 88 passes through a sensor 16 of the type described above, disposed in-line with the incoming flow of water. The sensor is configured to measure a colorimetric change of chemical reagents in the water in a reversible manner. The colorimetric change represents a value indicative of a degree of hardness of the incoming flow of water 88. The system 86 also includes a controller 94 that is configured to receive a signal indicative of the degree of hardness of the incoming flow of water 88 from the sensor 16. The controller 94 may also include a memory circuit 96 that is configured to relate a degree of concentration of a chemical species in the incoming flow of water 88 to a degree of hardness of the incoming flow of water 88, such as via a stored look-up table. The controller 94 is also configured to output a value indicative of the degree of hardness removed by the water softener to a comparator 98. The comparator 98 also includes an input for a signal indicative of capacity of an ion exchange resin 100 in the water softener. The comparator 98 is configured to compare the value indicative of the degree of hardness removed by the water softener with the capacity of an ion exchange resin 100, and to output a command for regeneration of the water softener.

Figure 7:
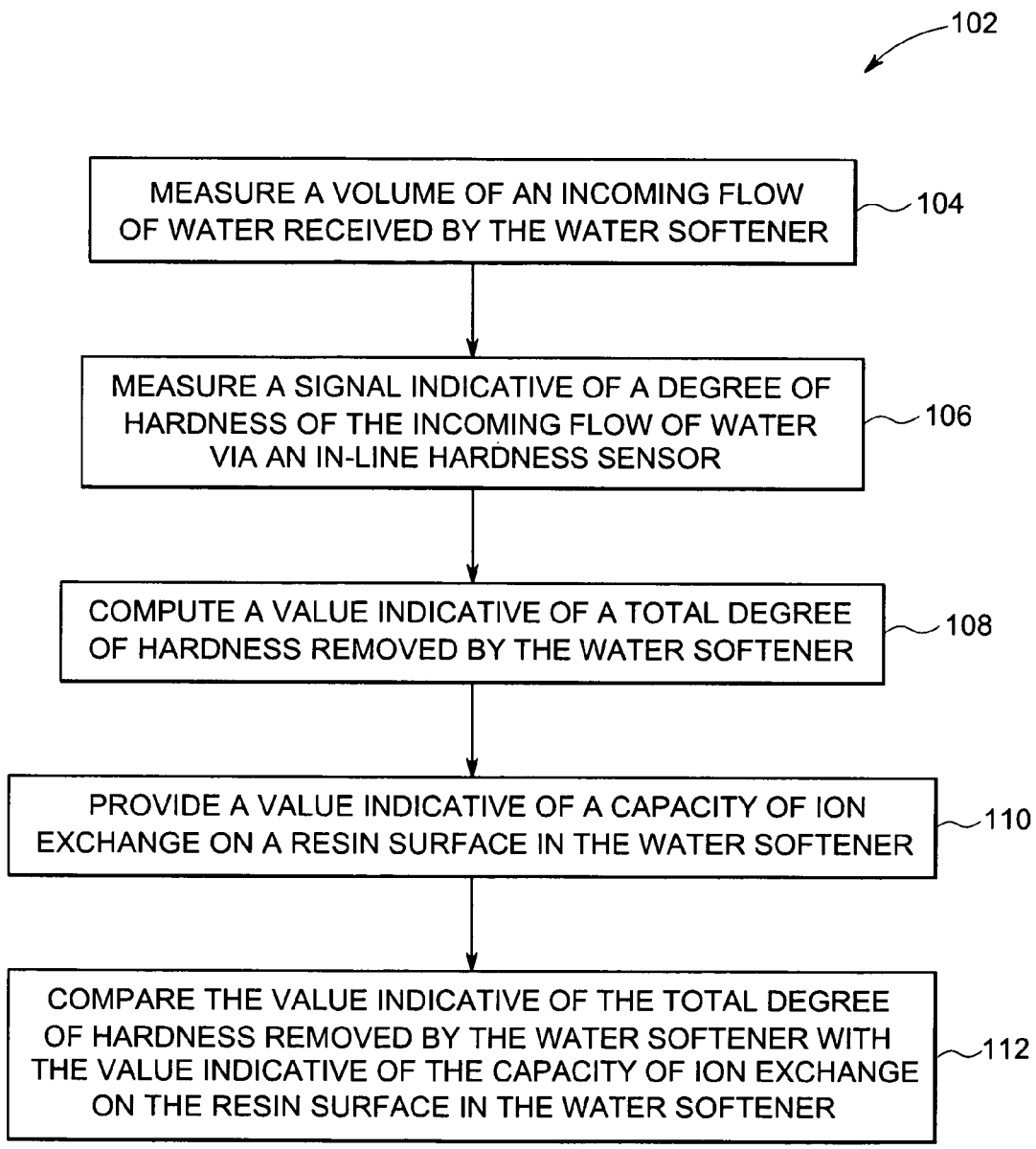
FIG. 7 is a flow chart illustrating exemplary steps for a method for controlling regeneration of the water softener of FIG. 6 in accordance with the invention.

FIG. 7 is a flow chart 102 illustrating exemplary steps for a method for controlling regeneration of a water softener in accordance with an embodiment of the present invention. The method includes measuring a volume of an incoming flow of water received by a water softener as step 104. After measuring the volume, a signal indicative of a degree of hardness of the incoming flow of water via an in-line hardness sensor is generated based upon hardness measured by the sensor, as indicated at step 106. A value indicative of a total degree of hardness removed by the water softener is then computed at step 108. This value is computed by multiplying the volume of incoming flow of water measured in step 104 by the degree of hardness measured in step 106.

The method 102 further includes providing a value indicative of a capacity of ion exchange on a resin surface in the water softener using specifications of the resin at step 110. The specifications of the resin include particular characteristics such as electrochemical and physical characteristics of the resin. The value indicative of the total degree of hardness removed by the water softener is compared with the value indicative of the capacity of ion exchange on the resin surface in the water softener at step 112 in order to output a command for regeneration of the water softener. A command for regeneration of the water softener is issued when the value indicative of the total degree of hardness removed by the water softener reaches the capacity of ion exchange on the resin surface in the water softener.

EXAMPLES

The examples that follow are merely illustrative, and should not be construed to be any sort of limitation on the scope of the claimed invention.

Figure 8:
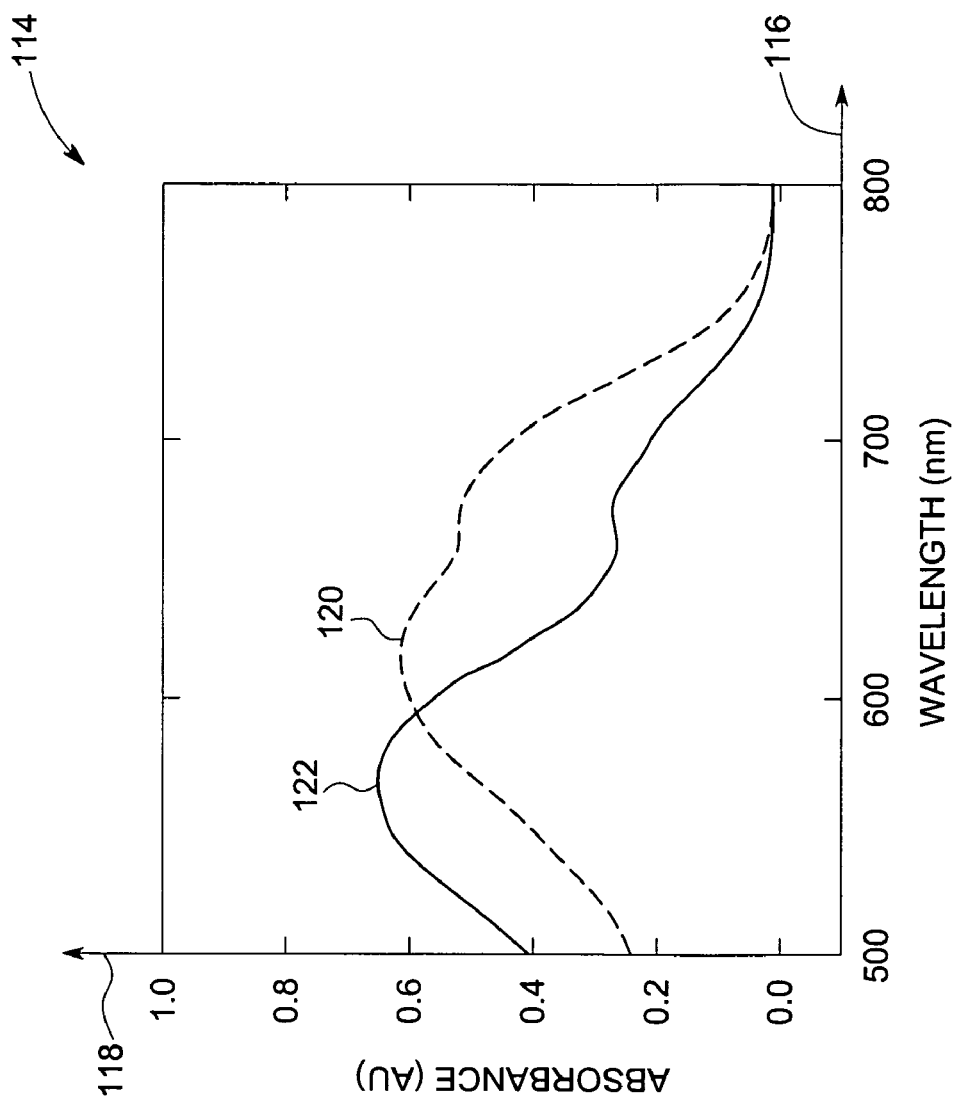
FIG. 8 is a graphical illustration of a spectral response of an eriochrome black T-based water hardness sensor of the type shown in the previous figures in response to exposure to a sample containing magnesium.

Experiments were performed using erichrome black T (EBT) as an indicator in a water hardness sensor. In addition, PEI was used as a pH modifier and poly 2-hydroxyethyl methacrylate was used as a sensing matrix. The thickness of a coating of the indicator, pH modifier and the sensing matrix was about 10 micrometers (em). A spectral response of the EBT-based water hardness sensor to exposure to a sample containing magnesium is illustrated in FIG. 8. The Y-axis designated generally by reference numeral 118 represents absorbance of magnesium and is dimensionless. The X-axis designated generally by reference numeral 116 represents wavelength of light in nanometers (nm). Plot 120 illustrates the absorbance of EBT-based water hardness sensor in a sample without magnesium, while plot 122 illustrates the absorbance of EBT-based water hardness sensor in a sample containing 75 parts per million (ppm) calcium carbonate equivalents of magnesium. It can be observed from the plots 120 and 122 that exposure to magnesium in the sample results in a decrease in absorbance at wavelengths greater than 600 nm and increase in absorbance at wavelengths shorter than 600 nm. This results in a change in color that may be reversible in the EBT indicator in response to addition of magnesium in the sample of water.

Figure 9:
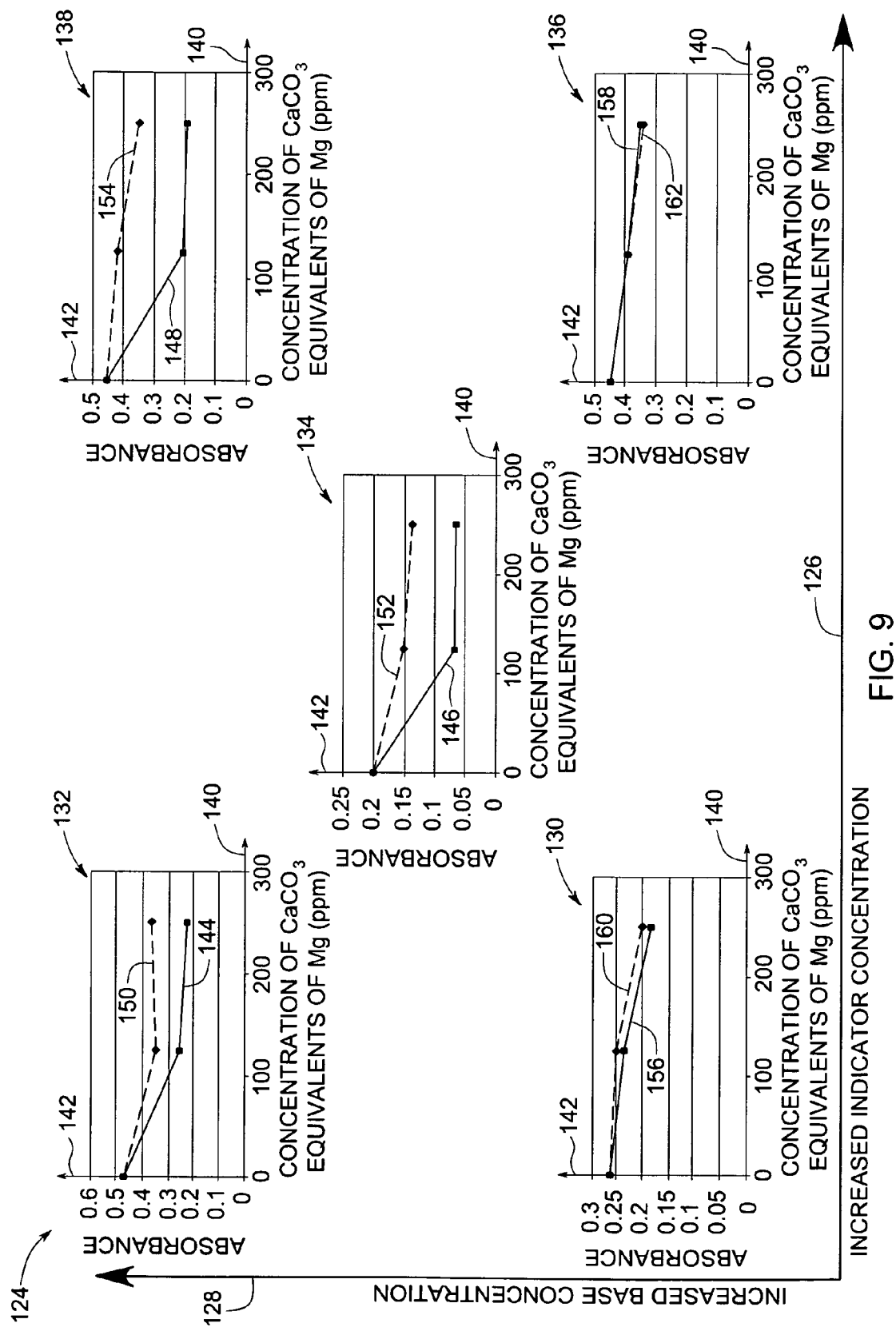
FIG. 9 is a graphical illustration of impact of concentrations of indicator and pH modifiers on sensitivity and selectivity of an Eriochrome black T-based water hardness sensor of the type shown in FIGS. 1 and 2 to calcium and magnesium.

FIG. 9 is a graphical illustration 124 of impact of concentrations of indicator and pH modifiers on sensitivity and selectivity of an EBT-based water hardness sensor to calcium and magnesium. The impact has been measured by plotting absorption changes at different values of concentrations of indicator and pH modifiers. The X-axis designated generally by reference numeral 126 represents indicator concentration and the Y-axis designated generally by reference numeral 128 represents pH modifier concentration. Response plot measurements made for different levels of modifier concentration and indicator concentration are illustrated in plots 130, 132, 134, 136 and 138. The X-axis of each of the response plots designated generally by reference numeral 140 represents the concentration of calcium carbonate equivalents of magnesium in parts per million (ppm) while the Y-axis designated generally by reference numeral 142 for each of the plots represents absorbance of light of the EBT-based sensor in response to calcium and magnesium species in water and is a dimensionless quantity.

Plot 130 is a response plot illustrating sensitivity to calcium and magnesium for a low value of indicator concentration and a low value of pH modifier concentration. Similarly, plot 132 is a response plot for a low value of indicator concentration and a high value of base concentration. Plot 134 is an absorbance spectrum for a medium level of indicator and base concentration. Further, plot 136 is a response plot for a high level of indicator and a low value of base concentration. Plot 138 is an absorbance spectrum for a high level of indicator concentration and a high level of base concentration. Absorbance measurements 144, 146 and 148 are made at elevated levels of modifier concentrations to illustrate response of the EBT-based sensor to magnesium show an enhanced sensitivity to magnesium relative to absorbance measurements 150, 152 and 154 that are made to measure sensitivity to calcium at the same levels of modifier concentration. Absorbance measurements 156 and 158 are made at low levels of modifier concentrations to illustrate response of the EBT-based sensor to magnesium show approximately equal sensitivity to magnesium when compared to absorbance measurements 160 and 162 that are made to measure sensitivity to calcium at the same levels of modifier concentration. Similarly, it can be seen from plots 148, 154, 158 and 162 that elevated indicator concentration results in enhanced sensitivity for both calcium and magnesium. Thus, elevated pH modifier concentration results in enhanced sensitivity to magnesium relative to calcium, while lower levels of pH modifier concentration generate approximately equal response in both cases.

Figure 10:
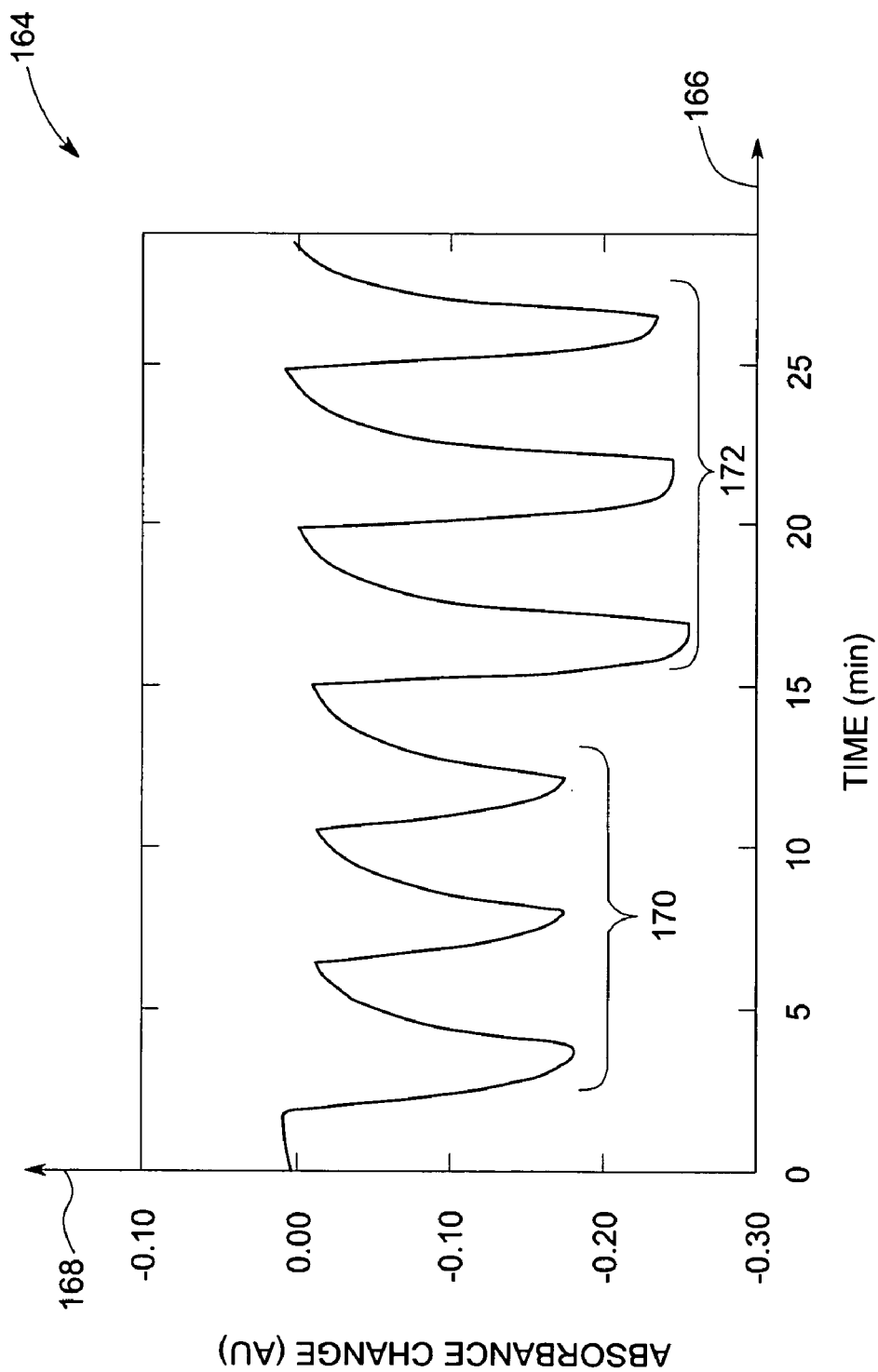
FIG. 10 is a graphical illustration of exposure of an eriochrome black T-based water hardness sensor of the type shown in FIGS. 1 and 2 to flowing streams of water containing varying concentrations of magnesium in real time.

FIG. 10 is a plot 164 of a real time response of EBT-based sensor to a sample of water containing varying amounts of magnesium. The X-axis, designated generally by reference numeral 166, represents time in minutes, while the Y-axis, designated generally by reference numeral 168, represents change in absorbance of the EBT-based sensor. As shown, the response 170 represents absorbance signal change as a result of the repetitive (triplicate) exposure of the sensor to 125 ppm calcium carbonate equivalents of magnesium resulting in a decrease in absorbance. Each exposure was followed by exposure of the sensor to deionized water that resulted in a return of the absorbance signal to a baseline value. Similarly, the response 172 represents absorbance signal changes as a result of the repetitive (triplicate) exposure of the sensor to 250 ppm calcium carbonate equivalents of magnesium resulting in a greater decrease in absorbance. Each exposure was followed by exposure of the sensor to deionized water that resulted in a return of the absorbance signal to a baseline value. Absorbance is normalized to a signal generated at 0 ppm calcium carbonate equivalents of magnesium. It is observed that the EBT-based sensor exhibited rapid response times of about 60 seconds to about 120 seconds for varying concentrations in magnesium in the water. Thus, a complete reversal of color change due to the varying concentrations in magnesium required, in the embodiment tested, about 60 to 120 seconds. This demonstrates the reversible nature of the EBT-based sensor.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A sensor comprising:
   a substrate;
   a sensing element disposed on the substrate, the sensing element consisting of a single layer and including a sensing matrix, an indicator for one or more chemical species in a flow of water, and a selectivity component that reacts reversibly with the one or more chemical species, the sensing matrix being in contact with the flow of water during operation;
   a light source configured to direct light through the substrate and the sensing element; and
   a light detector configured to receive transmitted light from the substrate and the sensing matrix and to generate a signal representative of selective wavelengths of the light indicative of the one or more chemical species in the flow of water.

2. The sensor of claim 1, wherein the selectivity component comprises a modifier that adjusts internal pH of the sensing element.

3. The sensor of claim 1, wherein the selectivity component comprises a chelator to selectively alter response of the sensing element towards a specific chemical species.

4. The sensor of claim 3, the chelator comprising 8-hydroxyquinoline.

5. The sensor of claim 1, wherein the substrate comprises a polymer or glass.

6. The sensor of claim 1, the indicator comprising at least one of calmagite, eriochrome black T, xylidyl blue or murexide.

7. The sensor of claim 1, the one or more chemical species comprising calcium and magnesium.

8. The sensor of claim 1, the sensing matrix comprising at least one of sol-gel, a polymer or a hydrogel.

9. The sensor of claim 1, the sensor configured to measure multiple wavelengths of light.

\* \* \* \* \*